United States Patent [19]

Stehman et al.

[11] 4,334,153
[45] Jun. 8, 1982

[54] X-RAY TUBE GRID BIAS SUPPLY

[75] Inventors: Harold E. Stehman, Hales Corners; Herbert E. Daniels, Brown Deer, both of Wis.

[73] Assignee: General Electric Company, Schenectady, N.Y.

[21] Appl. No.: 191,789

[22] Filed: Sep. 29, 1980

[51] Int. Cl.³ .................... H05G 1/00; H05G 1/34
[52] U.S. Cl. .................................... 250/405; 250/403
[58] Field of Search ............... 250/416 TV, 403, 405, 250/404

[56] References Cited

U.S. PATENT DOCUMENTS

| | | | |
|---|---|---|---|
| 1,567,012 | 12/1925 | Pilon | 250/403 |
| 1,946,286 | 2/1934 | Kearsley | 250/403 |
| 2,146,889 | 2/1939 | Franke et al. | 250/405 |
| 2,798,963 | 7/1957 | Saget | 250/405 |
| 3,916,202 | 10/1975 | Heiting et al. | 250/403 |

Primary Examiner—Alfred E. Smith
Assistant Examiner—T. N. Grigsby
Attorney, Agent, or Firm—Wheeler, House, Fuller & Hohenfeldt

[57] ABSTRACT

An adjustable focus x-ray tube has its cathode connected to the negative side of a dc power supply which is below ground by half of the total voltage applied to the tube and its anode connected to the positive side of the supply which is above ground by half of the applied voltage. A voltage divider is connected between the negative side or cathode and ground and an intermediate point on the divider is connected to a focusing electrode in the x-ray tube for providing a focusing bias voltage. Since the bias voltage is derived from the cathode-to-ground voltage it will always track or remain proportional to the cathode voltage so the effect of variations in the latter on focusing will be negated.

5 Claims, 3 Drawing Figures

X-RAY TUBE GRID BIAS SUPPLY

BACKGROUND OF THE INVENTION

This invention relates to a bias voltage supply for controlling an adjustable focus x-ray tube. The new bias supply is especially useful for controlling x-ray tubes in which the focal spot is reduced below the size normally available in conventional x-ray tubes to permit diagnostic procedures requiring high resolution radiography.

Conventional x-ray tubes used for medical diagnostic purposes are customarily provided with means for selecting the operating characteristics such as the anode to cathode voltage, the electron beam current, the focal spot size and the conduction or exposure time interval. The x-ray tube usually has an electrode, called a grid or a cup, to shape the electric field around the electron emitting filament for controlling the beam cross section so that a suitable focal spot is formed on the anode target. The control electrode is operated at cathode potential for full electron beam current and is biased negatively when electron beam cut-off is desired. The operating parameters of the tube, that is the maximum permissible combination of anode voltage, beam current and exposure time interval are normally coordinated in a manner that prohibits loading the target to the extent that melting might occur in the focal spot region of the target. Typically, the minimum focal spot size is limited to about 1.2 mm for conventional radiography.

For some diagnostic procedures such as brain or neurological examinations, the radiologist must be able to distinguish very fine details in the x-ray image so a high resolution radiography procedure must be adopted which means that a finer focal spot than is obtainable in a conventional general purpose x-ray tube must be used. High resolution or microfocus x-ray tubes have been developed for this purpose. These tubes have a second electrode intervening between the first electrode and the anode target for augmenting focusing. In some prior art systems, the second control electrode is connected to a variable bias voltage supply which permits making the second control electrode less negative, but not positive, with respect to the cathode for increased focusing. Unfortunately, as focus is adjusted in such tubes, electron beam current also changes undesirably and unpredictably. Another disadvantage of prior art systems results from the focusing electrode bias voltage being derived from a source that is independent of the cathode voltage of the tube so bias and, hence, the amount of focusing may vary independently with power line fluctuations and other transients during x-ray exposures which may endure for 1 millisecond to 6 seconds, by way of example.

U.S. Pat. No. 3,916,202, owned by the assignee of this application, discloses a variable microfocus x-ray tube wherein the second control or focusing electrode may be biased positive with respect to the cathode to obtain maximum focusing without having current flow to the control electrode as would be expected if positive bias voltage is used. This patent discloses use of two independent bias supplies which are connected through a two-pole switch to the second and first control electrodes, respectively such that when the tube is being used for making an x-ray exposure, a positive bias voltage is applied to the second focusing electrode and the focusing cup is connected to the filament and is at the same potential. To terminate an exposure, the positive supply is disconnected by the switch and the negative bias voltage supply is connected to both the first and second control grids to make the tube nonconductive. However, during an exposure interval, with the bias voltages derived from a source independent of the voltage applied to the x-ray tube, the tube is still vulnerable to focal spot size variations because of the second control grid voltage failing to track variations in the voltage applied between the anode and cathode of the tube which might result from power line voltage fluctuations, transients, impedance changes with load, and waveform variations.

SUMMARY OF THE INVENTION

In accordance with the invention, the problems of having the bias voltage on the second focusing or control electrode fluctuate due to variations in the waveform or level of the voltage applied between the anode and cathode of the tube are overcome by deriving a bias voltage for the second control electrode from the cathode voltage such that the bias voltage is always proportional to the cathode voltage. In other words, the focusing electrode bias voltage tracks the cathode voltage in real time so the degree of the electron beam focusing remains constant while an x-ray exposure is in progress.

Briefly stated, in the illustrated embodiment, the voltage which is to be applied between the cathode and anode of the x-ray tube is obtained from a rectifier that is fed from the delta-wye secondary of a three-phase transformer. A single-phase supply could be used, of course. There are two rectifier bridges having output terminals between which the cathode and anode of the x-ray tube are connected. The interconnection between the bridges is grounded and is at cathode-to-anode midpoint potential. The positive high voltage output line is connected to the x-ray tube anode. Thus, the absolute value of the positive anode voltage above ground potential is equal to the voltage by which the cathode is below ground potential. The bias voltage for the focusing electrode is derived from a circuit which connects between the negative line or cathode voltage line and ground so that if there is any variation in cathode voltage the bias voltage will vary in the same proportion and the net biasing effect will not change.

A further feature of the new bias circuit is that it provides high voltage dividers which permit monitoring, by oscilloscope or peak reading kilovoltage meters, the cathode-to-ground voltage and the focus electrode-to-ground voltage so that the difference between these voltages provides a measure of the bias voltage which is actually being applied to the second focusing electrode in respect to the cathode. In an alternative embodiment of the invention, this difference voltage is continuously sensed and compared with a reference voltage for producing a signal for operating a servo motor that is operative to lock-in the focal spot size during an exposure.

How the foregoing and other more specific objects of the invention are achieved will be evident in the detailed description of illustrative embodiments of the invention which will now be set forth in reference to the drawings.

DESCRIPTION OF A PREFERRED EMBODIMENT

A suitable microfocus x-ray tube to which the bias voltage system may be applied is described and illustrated in U.S. Pat. No. 3,916,202 which is incorporated herein by reference.

Figure 1:
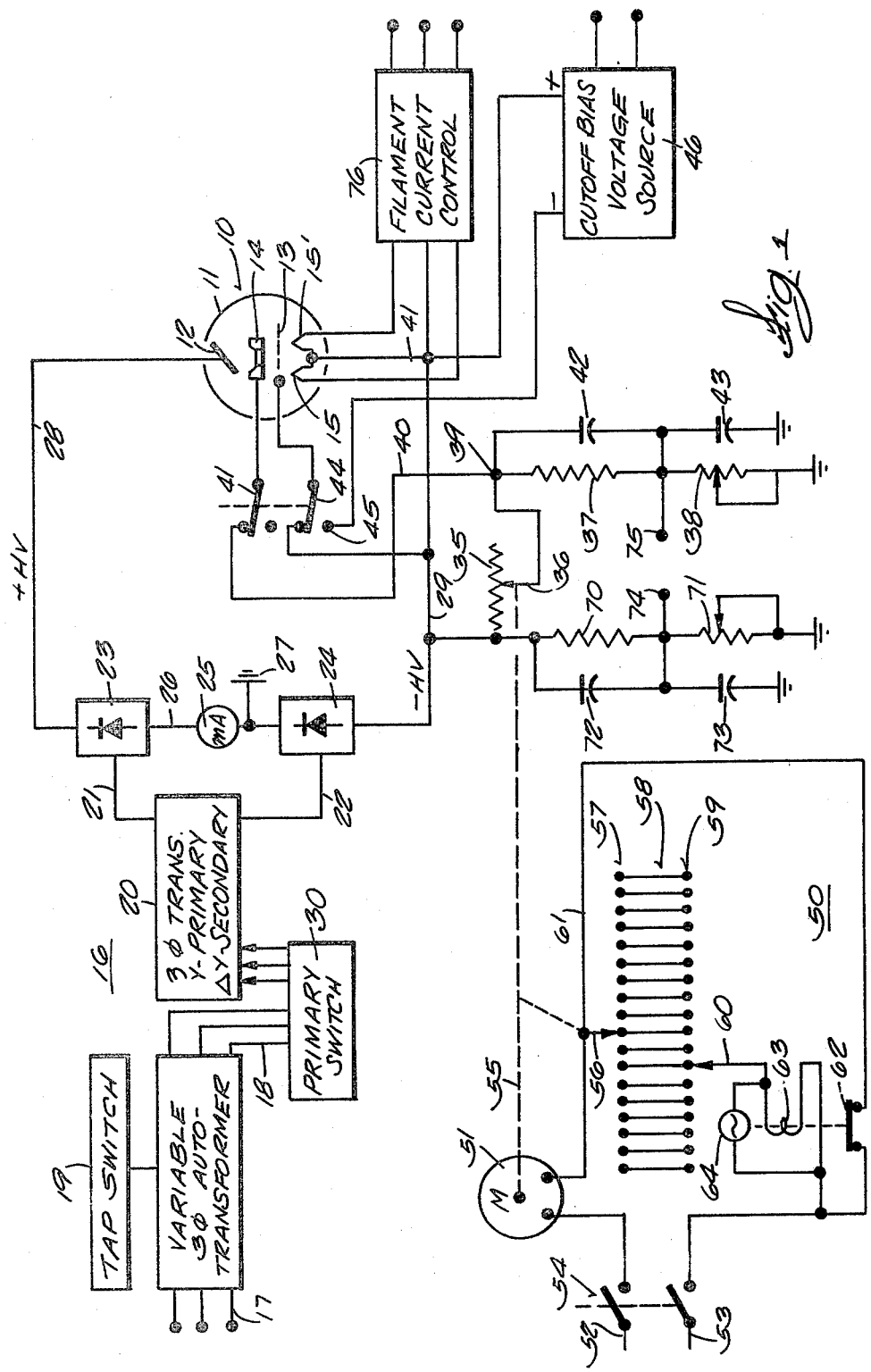
FIG. 1 is a diagram, partially schematic and partially in block form, of an x-ray tube power supply in which the new focusing bias voltage control is used.

Referring to FIG. 1, the x-ray tube is designated generally by the reference numeral 10. It comprises an evacuated envelope 11, an anode or target 12, a first control grid or electrode 13, a second fine-focusing electrode 14 and a pair of high and low emissivity filaments which are part of the cathode and are identified by the reference numerals 15 and 15'.

The high kilovoltage for being applied between cathodic filaments 15, 15' and anode target 12 is derived from a power supply which is generally designated by the reference numeral 16. A three-phase power supply is used in this example. It comprises a variable autotransformer represented by the block which is marked with this legend. The autotransformer is provided with tap switches for selecting its output voltage and these switches are symbolized by the block marked 19. The output lines 18 from the autotransformer lead to the terminals of the wye-connected primary winding of a three-phase transformer which is symbolized by the block marked 20. Transformer 20, in this example, has delta and wye secondary windings whose output lines are marked 21 and 22. Typically, ac voltages up to 150 kilovolts are obtainable between output lines 21 and 22 by making the necessary tap selection on the autotransformer.

A pair of full wave rectifier bridges 23 and 24 are supplied from the secondary of transformer 20. The line between these bridges includes of milliameter (mA meter) 25 which is at ground potential by virtue of the interconnecting line 26 being connected to ground at 27. Thus, one of the dc high voltage supply lines shown connected to the anode 12 of tube 10 is marked +HV and with the numeral 28 is at one-half of the total output voltage of the rectifier bridges above ground potential while the other dc output line marked −HV and 29 is at one-half of the total voltage below ground potential. By way of example, the maximum voltage on line 28 in a typical diagnostic x-ray system might be 75 kilovolts above ground while the voltage on line 29 would be 75 kilovolts below ground potential such that the total voltage between anode 12 and the cathodic filaments 15, 15' to which positive line 28 and negative line 29, respectively are connected would be 150 kilovolts when the autotransformer is set to supply maximum voltage to the transformer. The switching circuit for selecting which one of filaments 15 or 15' is to be energized for providing a high or low electron beam current have been omitted for the sake of brevity. The power supply outlined thus far is well known in the x-ray art and need not be described in any greater detail. The main point of interest is that during an x-ray exposure, x-ray tube anode 12 is above ground potential by the same amount that the cathodic filaments 15, 15' are below ground potential.

In FIG. 1, a block marked 30 represents a switching circuit for energizing the primary winding of transformer 20 immediately before an x-ray exposure is taken and for deenergizing the transformer when an exposure is terminated. Any suitable switching circuit may be used such as one that uses silicon control rectifiers. Suitable switching circuits are well known in the x-ray art and need not be described in detail. One may note, however, that except during an exposure, the high voltage lines 28 and 29 have no voltage applied to them.

The new biasing circuit for making the focus control electrode 14 of the x-ray tube track or remain proportional to the cathode 15, 15' voltage is illustrated as comprising a variable resistor 35 having a movable contact 36, a fixed resistor 37 and an adjustable or trimming resistor 38. In an actual embodiment a selector switch, not shown, and several resistors are used in place of adjustable resistor 35 so resistance variations can be obtained in about 17 discrete steps instead of being continuously variable. The potential at a point 39 of the divider circuit is applied by way of a line 40 and a contact 41 of double-throw switch to focusing electrode 14. Switch contact 41 is shown in the position which it is in when an exposure is being made, that is, when the high kilovoltage is being applied across the anode and cathode of the x-ray tube 10. The lower end of adjustable trimming resistor 38 is connected to ground to the potential applied across the divider circuit including the focus bias voltage setting resistor 35, and resistors 37 and 38 is the negative high voltage or the voltage existing between line 29 and ground. Line 29 is, of course, at cathode potential since it is connected by way of common line 41 to the midpoint of the two cathodic filaments 15,15'.

Alternating current source voltage variations, waveform variations and different loadings of the circuits in the x-ray system may, of course, result in the −HV potential on line 29 varying during an x-ray exposure. Moreover, the amount of ripple in the rectified voltage applied between lines 28 and 29 can vary from time to time. The bias circuit negates the effect of these variations. Any change in the voltage level on negative high voltage line 29 will produce a corresponding proportional change in the bias voltage for focusing control electrode 14 at point 39 of the divider. The ratio of bias voltage to cathode voltage remains constant so the degree of focus remains constant. In other words, the bias voltage on the focusing or second control electrode 14 is compelled to track the cathode voltage under all conditions during an exposure. The amount of focusing desired is established by adjusting the slider 36 on variable resistor 35 which, of course, causes a biasing voltage change at point 39 and at the focus control electrode 14 in reference to the cathode voltage. Resistors 37 and 38 in the focus control divider have smoothing capacitors 42 and 43, respectively, connected in parallel with them.

The first control grid 13 in the x-ray tube performs in a more or less conventional manner. During an exposure, switch contact 44 of the double-throw switch, which includes contact 41, is in the position in which it is shown in FIG. 1. When in this position, first grid 13, which is actually the focusing cup, is connected directly to the midpoint of the filaments 15, 15'. This puts the first control electrode 13 at filament or cathode voltage during an exposure. When an exposure is terminated switch 44 is transferred to connect with contact 45 on which there is a negative bias voltage applied by means of a cutoff bias voltage source indicated by the block marked 46. The cutoff bias voltage is generally on the order of a few thousand volts for the control grid 13 relative to the filaments 15, 15′.

When an exposure is being terminated, switch contact 41 of the double-throw switch opens to remove the biasing potential from second control or focusing electrode 14. The biasing potential on electrode 14 is positive with respect to the cathode voltage during an exposure. This electrode can be permitted to go positive relative to the cathode when the x-ray tube is conducting provided the tube has the properties of the tube described in cited U.S. Pat. No. 3,916,202. The characteristics of this tube will be discussed briefly later in reference to FIG. 3.

The position of the sliding contact 36 on the focus control resistor 36 could be selected manually and directly if a suitably calibrated scale were provided to indicate the percentage bias voltage which results from any position setting. A simple servo system, generally designated by the numeral 50, is provided for illustrating remote control of the slider 36 position. The servo system includes a motor 51 that is supplied from the power lines 52 and 53 when the two-pole switch 54 is closed. Motor 51 is coupled by means of a gear train, symbolized by the dashed line 55, to slider 36 for driving it. There is another slider 56 which moves on a series of contacts 57. Contacts 57 are connected by means of a multiconductor cable 58 to a corresponding set of contacts 59 which cooperate with a manually movable slider 60. Slider 60 is positioned manually to select the desired percentage of the cathode voltage which is to be applied as a biasing voltage to focusing electrode 14. In an actual embodiment, by way of example and not limitation, 18 pairs of contacts 57, 59 and a corresponding number of conductors 58 were used. This provided 17 bias voltage levels covering the range of 0 to 8% of the total x-ray tube voltage in 1.5% increments. However, an infinitely variable control could be used if desired.

In servo system 50, the operator selects a bias voltage by moving slider 60 to either side of the center point of resistor 35 depending on whether higher or lower focusing effect is desired. Inspection of the circuit will reveal that when slider 60 is in the position in which it is shown by way of example, a circuit is completed from power line 52, through motor 51, line 61, normally closed relay contact 62, and then back to power line 53. The motor runs under this condition and drives slider 36 correspondingly. In due course, motor driven slider 56 moves into alignment with manually positioned contact 60 in which case a relay coil 63 becomes energized to open contact 62 and stop the motor. An indicator lamp 64 then turns on under the influence of the voltage applied to relay coil 63 to indicate that the setting operation is complete and that an x-ray exposure may be made.

The circuit in FIG. 1 is provided with another voltage divider which is used to measure various voltages and is comprised of a fixed resistor 70 and an adjustable resistor 71. These resistors have filter capacitors 72 and 73 connected in parallel with them. The voltage drop across series connected divider resistors 70 and 71 between line 29 and ground is the x-ray tube cathode voltage and is the reference voltage. Thus, a voltage proportional to cathode voltage can be measured from a test point 74 and ground. Similarly, a voltage proportional to the bias voltage on focusing electrode 14 can be measured between a test point 75 on the other divider and ground. These voltages may be measured with a peak reading volt meter or an oscilloscope and subtracted from each other such that the difference is the actual bias voltage on the second control and focusing electrode 14. Thus, the focusing bias voltage can be continuously monitored.

In FIG. 1, the filament current control is represented by the block marked 76 and may be considered to be conventional in that anyone skilled in x-ray circuit design will be able to devise a suitable control. It is sufficient to remark here that different voltages can be applied to the individual filaments 15 and 15′, respectively, for increasing or decreasing their emissivity and, hence, the electron beam current that flows through the x-ray tube during an exposure. As has been pointed out earlier, the tube current is measured by mA meter 25 which is actually in a series circuit between the cathode and anode of the x-ray tube.

Before describing a further development of the invention illustrated in FIG. 2, a suitable dual control electrode adjustable focus x-ray tube for using the new self-compensating biasing voltage supply will be described in reference to FIG. 3. The tube elements shown in that FIGURE are described in greater detail in previously cited U.S. Pat. No. 3,916,202.

Figure 3:
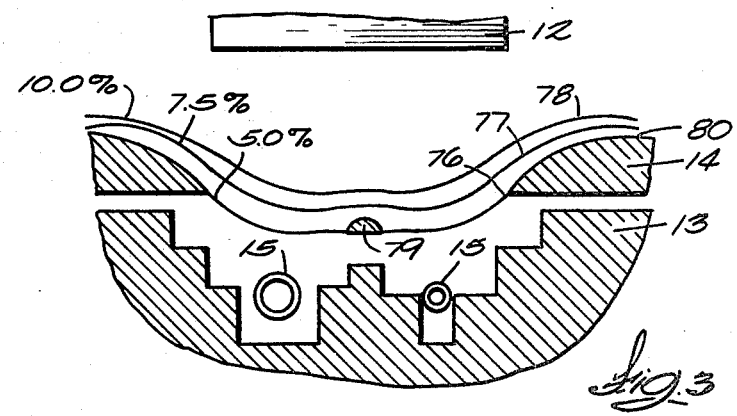
FIG. 3 is a fragmentary section of the cathode including the filaments and focusing cup or first biasing electrode in conjunction with a second focusing electrode and an anode comprising a typical x-ray tube to which the new focusing bias voltage control may be applied.

In FIG. 3, parts which have been previously identified in connection with FIG. 1 are given the same reference numerals. Thus, the two coils of filament wire 15 and 15′ are depicted. Each filament is in a recess of the focusing cup 13 which corresponds with focusing and cutoff bias applying electrode 13 in FIG. 1. As explained earlier, when the x-ray tube is conducting, control electrode 13 is connected directly to filaments 15 and 15′ to create an electric field which aids in focusing the electron beam. On the other hand, to terminate or cut off an exposure, electrode 13 is disconnected from the filaments and connected to a negative cutoff bias voltage source 46 to prevent the x-ray tube from conducting. Focusing electrode 14, called a lens-grid in the cited patent, is shown fragmentarily in FIG. 3. As explained in great detail in the cited patent, the configuration and location of the focusing control electrode 14 is such that bias current will not flow through this electrode even if it becomes positive as it does relative to the cathode constituted by the filaments 15 and 15′ and cathode cup or grid 13. An appropriate tube for use with the focusing bias circuit described herein is one that allows the focusing electrode to become positive relative to the cathode or filaments without having bias current flow through it.

Whenever there is a high dc voltage applied between the x-ray tube filaments and anode target 12, discrete equipotential field lines exist. Three of the lines corresponding with 5.0%, 7.5% and 10% of cathode-to-anode voltage are illustrated in FIG. 3 and, besides being marked with a definite percentage, are further identified by the reference numerals 76, 77 and 78. There is a focusing recess dividing rod 79 spanning across the focusing cup recess to isolate the electric fields created by the potential on the individual filaments. In FIG. 3, the typical solid equipotential lines 76-78 are those that exist when the lens-grid or focus control electrode 14 is biased to a potential equal to the equipotential value of the line that coincides with the contour of electrode surface 80. When this condition exists, the electron beam emitted from either of the cathode filaments 15 or 15' will focus on the surface of anode target 12 with a predetermined focal spot size and the trajectory of the electron will not be affected by the selected equipotential. In FIG. 3, the particular equipotential at the surface 80 of focusing electrode 14 just happens to represent the case where about 5% of the cathode-to-anode voltage is applied between lens-grid electrode 14 and the filaments 15 and 16. The 5% equipotential line is located at about the middle of the zero to 8% of the total tube voltage used in an actual embodiment as was mentioned earlier. Ideally, focusing electrode 14 should be moved in accordance with the biasing voltage selected to place its contour top surface 80 at the percentage equipotential line that coincides with the selected biasing voltage. It is not practical to do this, of course, but as long as the surface 80 of the electrode 14 is at about the midpoint in the range of biasing potentials that are to be selected, no significant grid current will flow through this electrode nor will any be subtracted from the electron beam. Hence, electron current flow from the cathode to the anode in the x-ray tube is independent of the unaffected by the level of the focusing electrode 14 bias voltage.

A further development of the invention will now be described in reference to FIG. 2 wherein parts which are similar to those depicted in FIG. 1 are given the same reference numerals. In this FIGURE, the ac transformer power supply and rectifier components are omitted but the high voltage dc lines 28 and 29 and the ground connection 27 are shown. The bias voltage for focusing electrode 14 is taken off of the divider at the same point 39 as in FIG. 1. The divider, consisting of resistors 70 and 71 for determining x-ray tube cathode potential relative to ground is the same.

Figure 2:
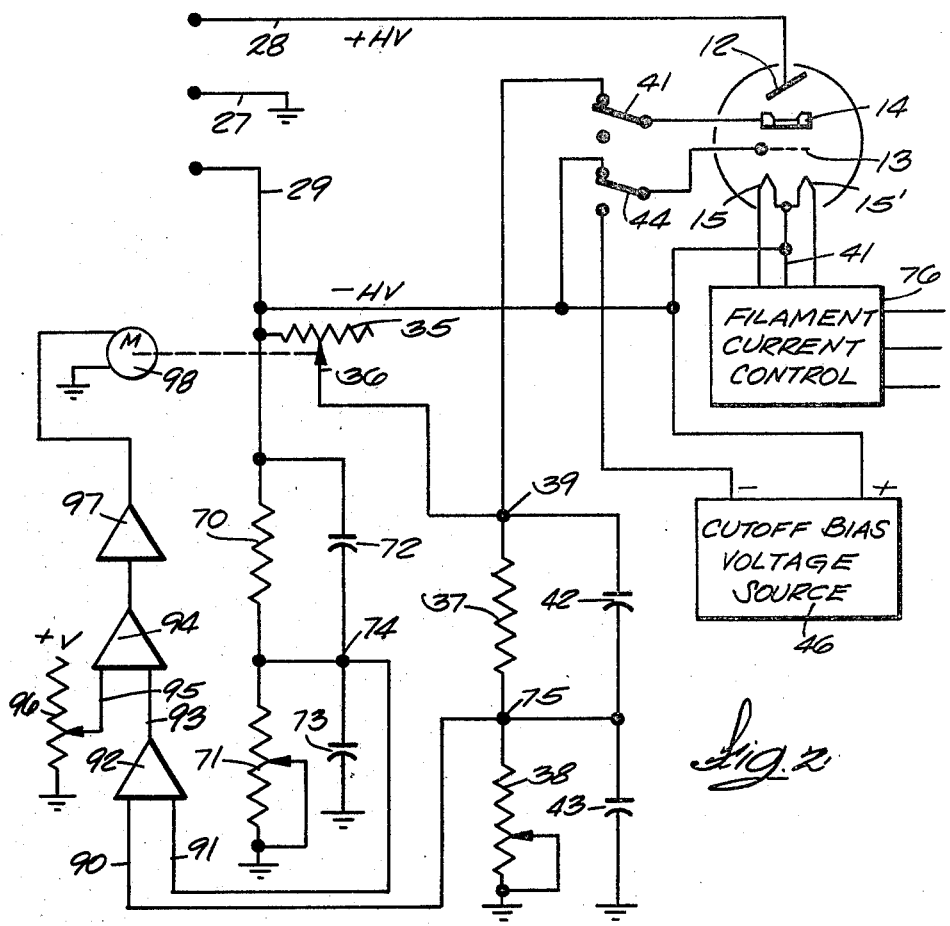
FIG. 2 is an alternative embodiment of the bias control circuit with some parts depicted in the previous figure omitted.

In the FIG. 2 embodiment, however, the difference potential existing between test points 74 and 75, which potential is the actual potential between focusing electrode 14 and the x-ray tube cathode, is used as a feedback signal to lock in the focal spot size during an exposure. As indicated earlier, exposure intervals are typically in the range of 1 ms to 6 seconds.

In FIG. 2, a signal equal to the focus control electrode bias voltage between points 74 and 75 is applied by way of lines 90 and 91 to the inputs of an operational amplifier 92. The resulting amplified signal on the output amplifier 92 constitutes an input by way of line 93 to a comparator amplifier 94. The other input 95 to comparator 94 is a reference voltage derived from a potentiometer 96 which is adjusted to set desired bias voltage on focusing electrode 14. The output of comparator 94 is fed to a servo amplifier 97 which supplies power to a motor 98 that is mechanically coupled to the slider 36 of resistor 35 in the focusing electrode biasing divider. Thus, in this case the focus or bias voltage is selected by adjusting potentiometer 96 which will cause motor 98 to run until slider 36 reaches a position which produces the desired bias voltage across terminals 74 and 75 in which case equilibrium is reached and motor 98 stops. Now, when the x-ray tube is turned on, if there is any fluctuation in the applied voltages which would tend to cause a fluctuation in the bias voltage on focusing electrode 14, motor 98 will drive and make a resistance correction to reestablish the equilibrium that was set by adjusting potentiometer 96. In other words, a voltage fluctuation will cause the comparator to produce an output signal which results in the motor 98 being energized until the comparator 95 becomes balanced again.

Although implementations of the concept of causing a bias voltage to track or vary in proportion to x-ray tube cathode voltage have been described in detail, such description is intended to be illustrative rather than limiting, for the invention may be variously embodied and is to be limited only by interpretation of the claims which follow.

We claim:

1. A system for providing a variable bias voltage for an x-ray tube that is adapted for varying its focal spot size, said tube comprising a target anode, cathode means spaced from the anode and including a filament and a first control electrode proximate to the filament, and a second electrode for controlling focusing located between said cathode means and said anode, means for connecting said anode to the positive terminal of a dc kilovoltage supply which is above ground by a predetermined amount and means for connecting said filament of said cathode means to the negative terminal of said supply which is below ground by a predetermined amount, and the improvement for applying to said second electrode a focus control bias voltage which will vary in proportion to any variations in the applied kilovoltage between said cathode means and ground when said x-ray tube is conducting such that said bias voltage will track said applied kilovoltage, comprising:

a first voltage divider means including at least two resistor means connected in a series circuit, at least one of which has means for adjusting its value for selecting bias voltage level, connected between said cathode means and ground, and means for connecting a point intermediate of said resistor means to said second electrode to provide the bias voltage for focusing.

2. The system defined in claim 1 wherein:

said voltage divider series circuit includes an adjustable resistor connected between another resistor in said circuit and ground for establishing a point intermediate of said resistors at which the voltage in respect to ground is proportional to the bias voltage on said second electrode in respect to ground, another voltage divider means including at least two resistors connected in a series circuit between said cathode means and ground, one of said resistors being connected between the other resistor and ground for establishing a point between said resistors at which the voltage in respect to ground is proportional to the voltage of said cathode with respect to ground such that the difference between the voltages at said points on the respective dividers will be representative of the bias voltage between said second electrode for focusing and said cathode means.

3. The system defined in any of claims 1 or 2 including:

a bias voltage source for said first electrode having negative and positive output terminals, a circuit including switch means which when in a first state connects said negative terminal of said bias voltage source to said first electrode to effect cutoff of electron emission from said filament and disconnects said focusing second electrode from said intermediate point in said first voltage divider means and which when in a second state connects said focusing electrode to said point, disconnects said first electrode from said negative terminal and connects said first electrode to said filament.

4. The system defined in any of claims 1 or 2 wherein the resistance in said first divider means is selectable to permit obtaining a bias voltage on said second electrode for focusing which is in the range of zero to about 8% of the voltage applicable between the cathode and anode of said x-ray tube.

5. The system defined in claim 2 including means for locking in the focal spot size of the x-ray tube during an exposure comprising:

means for sensing the voltage difference between the points on each divider which represents the bias voltage applied between the x-ray tube focusing electrode and cathode, means operative to compare the sensed bias voltage with a selectable reference voltage that corresponds with the bias voltage for the amount of focusing desired and to produce a signal representative of the difference between the sensed and selected voltage, motor means responsive to said signal by adjusting said resistor means in said first voltage divider until the difference is nulled.

* * * * *